United States Patent [19]

Kwon et al.

[11] Patent Number: 5,319,106

[45] Date of Patent: Jun. 7, 1994

[54] STABILIZATION OF MIXTURES OF MALEIC ANHYDRIDE AND ACRYLIC ACID DURING DISTILLATION

[75] Inventors: Joon T. Kwon, Freehold; Joseph W. Stanecki, Boonton, both of N.J.

[73] Assignee: ABB Lummus Crest Inc., Bloomfield, N.J.

[21] Appl. No.: 978,260

[22] Filed: Nov. 9, 1992

[51] Int. Cl.$^5$ ............................................. C07D 307/36
[52] U.S. Cl. .................................. 549/262; 203/8; 203/9
[58] Field of Search ..................... 549/262; 203/8, 9

[56] References Cited

U.S. PATENT DOCUMENTS

| | | | |
|---|---|---|---|
| 3,725,208 | 4/1973 | Maezawa et al. | 203/8 |
| 4,021,310 | 5/1977 | Shimizu et al. | 203/8 |
| 4,465,881 | 8/1984 | Miller et al. | 203/8 |
| 4,511,670 | 4/1985 | Suciu et al. | 502/209 |
| 4,594,433 | 6/1986 | Suciu et al. | 549/256 |
| 4,654,425 | 3/1987 | Suciu et al. | 549/256 |
| 4,754,058 | 6/1988 | Levy | 560/205 |

OTHER PUBLICATIONS

Kanabara et al., CA 108(26):222261y (1988).
CA 105(10):79510j (1986).
Haley et al., CA 96(6):35918q (1981).
Brown et al., CA 76(26):154394n (1972).
75(1):5266z (1971).
Day et al., CA 111(8):58500q (1989).
D. A. DeMaio, "Will Butane Replace Benzene As A Feedstock For Maleic Anhydride?", Original published May 19, 1980, pp. 114–116 of unknown publication.

*Primary Examiner*—Cecilia Tsang
*Attorney, Agent, or Firm*—Chilton, Alix & Van Kirk

[57] ABSTRACT

In the production of maleic anhydride, a crude maleic anhydride is produced which contains acrylic acid and other by-products. The crude maleic anhydride is dissolved in a solvent and the acrylic acid is distilled off. To avoid the polymerization of the acrylic acid, an inhibitor of phenothiazine is added to the distillation process.

4 Claims, 2 Drawing Sheets

STABILIZATION OF MIXTURES OF MALEIC ANHYDRIDE AND ACRYLIC ACID DURING DISTILLATION

BACKGROUND OF THE INVENTION

This invention relates to a process for the production of maleic anhydride and particularly to the separation of resulting mixtures of maleic anhydride and acrylic acid by distillation so as to inhibit polymer formation.

In the process for producing maleic anhydride from butane or benzene by oxidation with air in the vapor phase, the resulting crude product contains not only the maleic anhydride but also carbon monoxide, carbon dioxide, steam, residual air, acetic acid, acrylic acid and various other heavy end products. The constituents which are noncondensable at the temperatures involved including the carbon monoxide, carbon dioxide, steam and residual air are vented. The condensables including the acetic acid, acrylic acid, the heavy ends and the maleic anhydride product are then condensed or extracted into a solvent such as water or organic solvents. The light ends, i.e. the acetic acid and the acrylic acid are distilled off from the maleic anhydride product and the heavy ends. In this distillation, the acrylic acid, which is now concentrated along with the acetic acid, can polymerize to form gums, resins and even solids which can plug the tower internals and transfer lines.

Hydroquinone monomethyl ether activated by dry air (oxygen) would normally be the inhibitor of choice to prevent this polymerization since it is used commercially when purifying crude acrylic acid to prevent polymerization. However, it has been found that its effectiveness as a polymer inhibitor is diminished when maleic anhydride is present, apparently due to the formation of a stable equimolar complex with maleic anhydride. Therefore, it was necessary to maintain the acrylic acid concentration of the distillate below 30 wt. % for the inhibitor to be effective. Dilution of the distillate is achieved by allowing the maleic anhydride concentration to increase, but this constitutes a loss of valuable product.

SUMMARY OF THE INVENTION

An object of the present invention is to provide a process by which the maleic anhydride product in a crude maleic anhydride stream containing acrylic acid can be separated from the acrylic acid while diminishing the potential for polymer formation. Specifically, the present invention involves the use of phenothiazine as a polymer inhibitor which permits higher concentrations of acrylic acid thereby improving the recovery of maleic anhydride and elimination of the need for activation air.

DESCRIPTION OF PREFERRED EMBODIMENTS

As generally known in the art, saturated or unsaturated $C_4$ to $C_{10}$ hydrocarbons or mixtures thereof are generally suitable as feeds for producing maleic anhydride. Examples are n-butane, butadiene, benzene, or a $C_4$ cut from a refinery. The n-butane is the preferred feed. The n-butane is oxidized to maleic anhydride usually in the presence of fluidized catalyst by reaction of the n-butane with oxygen at a temperature in the order of 320° C. to 500° C. The reaction is accomplished with an excess of oxygen with the oxygen usually being provided with an inert gas. This is usually done by using air. For examples of the production of maleic anhydride, see U.S. Pat. Nos. 4,594,433 and 4,654,425.

Figure 1:
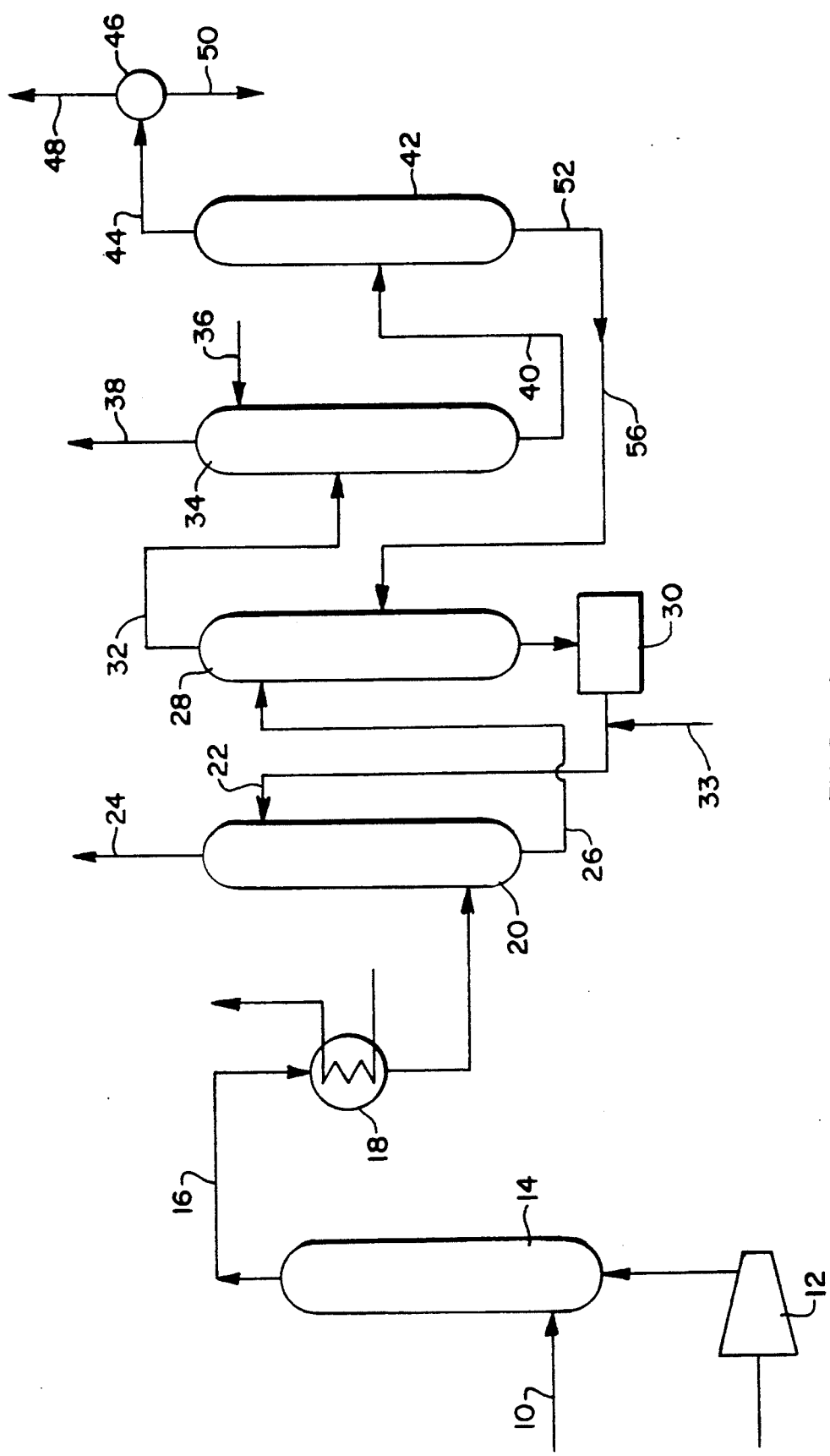
FIG. 1 is a flow diagram for a typical maleic anhydride production process incorporating the present invention.
Figure 2:
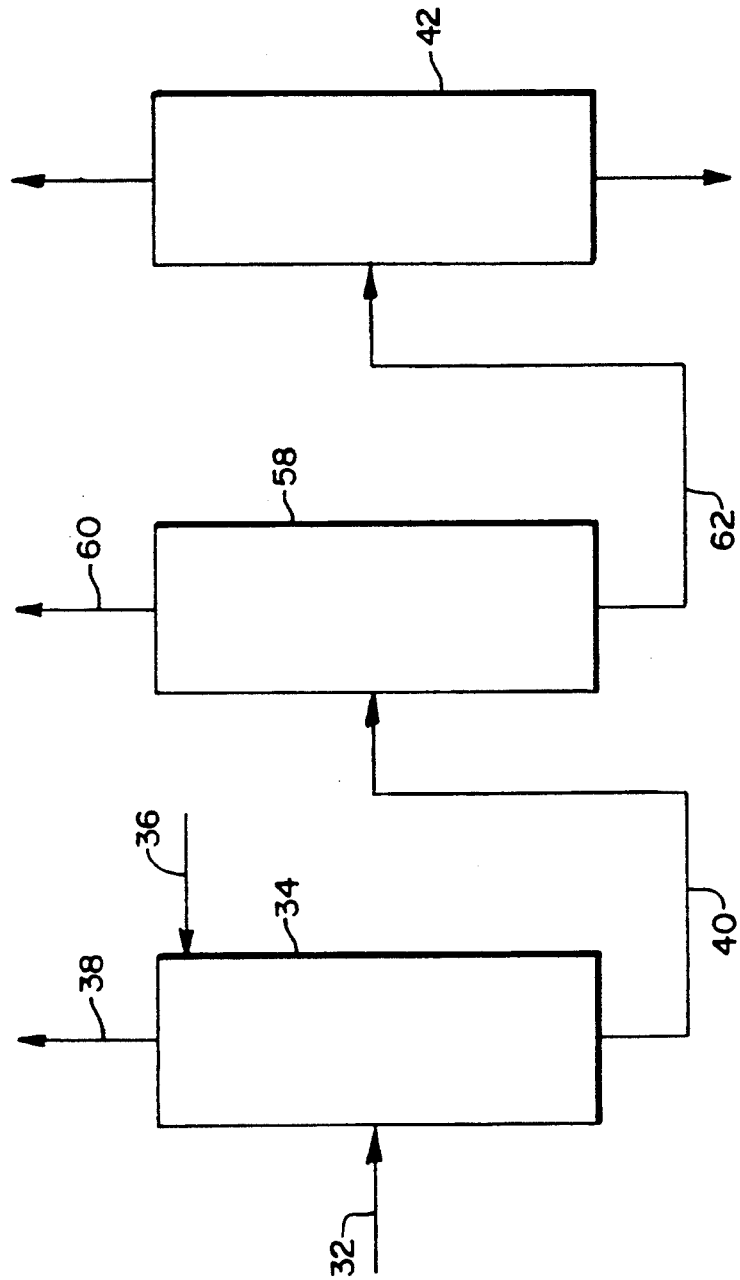
FIG. 2 is a flow diagram illustrating a modified embodiment of the present invention.

FIG. 1 illustrates the basics of a known maleic anhydride process with the addition of the present invention. The invention could just as well be applied to maleic anhydride processes having different specific process details. The specific process shown uses an organic solvent but the invention is also applicable to systems using an aqueous solvent.

The vaporized butane or benzene or other hydrocarbon feed 10 and the air from compressor 12 are fed into the catalytic reactor 14. This reactor 14 would include means (not shown) for removing the heat of reaction and means (also not shown) for handling and providing fresh catalyst. Also this reactor 12 could be a fixed bed reactor or a fluidized circulating bed reactor.

The crude product 16 from the reactor 14 contains not only the maleic anhydride but also excess air, carbon monoxide, carbon dioxide, acetic acid, acrylic acid and some heavy end products. The reaction products 16 are cooled in heat exchanger 18 and then passed to absorber 20. In absorber 20, the condensables, acetic acid, acrylic acid, heavy end products and maleic anhydride, are extracted into an organic solvent fed into the absorber via line 22. Examples of solvents which can be used include polymethyl benzophenones, dimethyl phthalate with phthalic anhydride and preferably a cycloaliphatic acid ester such as diisobutyl hexahydrophthalate. The non-condensables, residual air, carbon monoxide, carbon dioxide and steam, are vented at 24 preferably to a waste heat boiler (not shown).

The maleic anhydride product dissolved in the solvent together with the other non-condensables is fed via line 26 to the stripper column 28 which is a vacuum tower where solvent is removed as a bottoms product and the crude maleic anhydride is removed at the top. The solvent is then purified at 30, fresh solvent is added as needed at 33 and the solvent is returned to stripper 20 in line 22.

The crude maleic anhydride product which has been stripped of most of the solvent is fed from stripper 28 through line 32 to the light ends distillation column 34 where the acetic acid and acrylic acid are distilled off. It is at this point that the present invention comes into play. The acrylic acid along with the acetic acid which are concentrated in the light ends column can polymerize to form gums, resin and even solids. These polymerizaiton products can plug the column internals and the transfer lines. As previously indicated, a prior solution to this problem was the use of a hydroquinone monomethyl ether polymerization inhibitor. However, the use of that inhibitor creates the problems previously discussed making it less than ideal.

The present invention involves the use of phenothiazine as the polymerizaiton inhibitor. Because it remains active in the presence of maleic anhydride and does not form complexes with maleic anhydride, the required concentration of phenothiazine to effectively inhibit polymer formation is less than that required for hydroquinone monomethyl ether. Also, higher concentrations of acrylic acid are possible thereby improving the recovery of maleic anhydride. Further, since air (oxygen) is not needed to activate this inhibitor, the load on the vacuum producer is decreased resulting in a savings in utilities.

The phenothiazine inhibitor is fed into the light ends distillation column 34 through line 36. The phenothiazine is fed at a rate to give a concentration in the light ends column overhead 38 which is less than 200 ppm by wt. which is the concentration presently used for hydroquinone monomethyl ether. The concentration of the phenothiazine in the overhead 38 is preferably in the range of 50 to 100 ppmw. The phenothiazine can be added by dissolving it in maleic anhydride at 10 to 20 wt. % at 80° C. and then adding this solution to a reflux drum of column 34 at a rate which results in about 50 ppmw in the reflux. The overhead from the column 34 containing primarily the acrylic acid and the acetic acid are vented and may be sent to a thermal incinerator/waste heat boiler (not shown) along with the overhead from the absorber 20.

The bottoms from the column 34 containing the maleic anhydride, heavy end products, inbibitor and organic solvent are fed in line 40 to the product distillation column 42 where the maleic anhydride is distilled off from the heavy ends, organic solvent and inhibitor. The overhead is withdrawn at 44 with any non-condensables being separated at 46 and vented at 48 and with the final maleic anhydride product being withdrawn at 50. The bottoms 52 from the column 42 containing the heavy ends, the inhibitor and organic solvent are recycled at 56 to the stripper 28 as desired.

As previously mentioned, the present invention may be practiced using an aqueous solvent instead of an organic solvent. In this instance, a de-watering (solvent removal) step is employed between the light ends column 34 and the product column 42 in the distillation column 58. The solvent water is distilled off at 60 and the bottoms with most of the water removed are fed via line 62 to the product column 42.

Although certain details of particular maleic anhydride production processes have been described, the invention is applicable to maleic anhydride production process in general as defined by the claims.

We claim:

1. A maleic anhydride production process wherein a crude maleic anhydride is produced also containing acrylic acid and wherein said crude maleic anhydride is dissolved in a solvent and including the step of distilling said acrylic acid off from said dissolved maleic anhydride, the improvement comprising the step of introducing into said step of distilling off said acrylic acid a polymerization inhibitor consisting essentially of phenothiazine to prevent the polymerization of said acrylic acid.

2. In a maleic anhydride production process wherein a crude maleic anhydride is produced containing said maleic anhydride, acetic acid and acrylic acid and wherein said crude maleic anhydride is dissolved in a solvent and wherein said acetic acid and acrylic acid are removed from said dissolved maleic anhydride as an overhead in a distillation step, the improvement comprising the step of introducing into said distillation step a polymerization inhibitor consisting essentially of phenothiazine to prevent the polymerization of said acrylic acid.

3. In a maleic anhydride production process of claim 2 wherein said phenothiazine is introduced in an amount to give a concentration of phenothiazine in said overhead of less than 200 ppm by weight.

4. In the maleic anhydride production process of claim 3 wherein said phenothiazine is introduced in an amount to give a concentration of phenothiazine in said overhead of 50 to 100 ppm by weight.

* * * * *